(12) United States Patent
Johnson

(10) Patent No.: US 12,109,183 B2
(45) Date of Patent: Oct. 8, 2024

(54) METHODS AND COMPOSITIONS INCLUDING PROTOCATECHUIC ACID CRYSTALS FOR THE TREATMENT OF CONDITIONS CAUSED BY AN ENVELOPED VIRUS

(71) Applicant: Lanny Leo Johnson, Frankfort, MI (US)

(72) Inventor: Lanny Leo Johnson, Frankfort, MI (US)

( * ) Notice: Subject to any disclaimer, the term of this patent is extended or adjusted under 35 U.S.C. 154(b) by 0 days.

(21) Appl. No.: 17/453,432

(22) Filed: Nov. 3, 2021

(65) Prior Publication Data

US 2022/0054436 A1 Feb. 24, 2022

Related U.S. Application Data

(63) Continuation-in-part of application No. 16/947,256, filed on Jul. 24, 2020, now Pat. No. 11,266,145.

(51) Int. Cl.
*A61K 31/192* (2006.01)
*A61K 31/18* (2006.01)
*A61P 31/18* (2006.01)

(52) U.S. Cl.
CPC ............ *A61K 31/192* (2013.01); *A61P 31/18* (2018.01)

(58) Field of Classification Search
CPC .................................................. A61K 31/192
See application file for complete search history.

(56) References Cited

U.S. PATENT DOCUMENTS

| 10,959,969 | B1 | 3/2021 | Johnson |
| 2007/0154508 | A1 | 7/2007 | Patton et al. |
| 2008/0274163 | A1* | 11/2008 | Schwartz ............. A61K 9/0043 239/289 |
| 2013/0095240 | A1 | 4/2013 | Parekh et al. |
| 2018/0243309 | A1 | 8/2018 | Konowalchuk |

FOREIGN PATENT DOCUMENTS

| CN | 102151256 | * | 8/2011 | ............ A61K 31/192 |
| CN | 106770865 | B | 3/2018 | |
| WO | 2016124936 | A1 | 8/2016 | |

OTHER PUBLICATIONS

Bae et al. ("Investigation of *Brassica juncea*, Forsythia suspensa, and Inula britannica: phytochemical properties, antiviral effects, and safety," BMC Complementary and Alternative Medicine, 2019, 19, 253).*
Lee et al. ("Antiviral Effects of Black Raspberry (*Rubus coreanus*) Seed and Its Gallic Acid against Influenza Virus Infection," Viruses, 2016, 8, 157).*
PCT Written Opinion of the International Searching Authority, international appl. No. PCT/US2022/048688, issued Feb. 1, 2023.
PCT International Search Report, international appl. No. PCT/US2022/048688, issued Feb. 1, 2023.
C B Ou, et al., "Protocatechuic acid, a new active substance against the challenge of avian infectious bursal disease virus" Poult. Sci. 91(7):1604-1609 Abstract.
C B Ou, et al.,Erratum to "Protocatechuic acid, a new active substance against the challenge of avian infectious bursal disease virus" Poult. Sci. 91(7):1604-1609.
H.C Lee et al., "Effect of tea phenolics and their aromatic fecal bacterial metabolites on intestinal microbiota", Microbial. 2006, 157, 876-884, (Year: 2006).
Ilana Agmon, et al., "Spontaneous deformation of protocatechuic acid monohydrate crystals: crystallographic aspects", Proc. R. Soc. Lond. A 387, 3116330 (1983).
Jennifer Le, "Drug Administration", Drug Administration, Drugs Merck Manuals Consumer Version, Last full review/revision Oct. 2020, Content last modified Oct. 2020.
Sherif T. S. Hassan, Emil Švajdlenka, Kateřina Berchová-Bimová, "*Hibiscus sabdariffa* L. and Its Bioactive Constituents Exhibit Antiviral Activity against HSV-2 and Anti-enzymatic Properties against Urease by an ESI-MS Based Assay", Molecules, May 2017; 22(5): 722.
Joshua A. Jackman, Pei-Yong Shi, Nam-Joon Cho, "Targeting the Achilles Heel of Mosquito-Borne Viruses for Antiviral Therapy", ACS Infect. Dis. 2019, 5, 4-8, DOI: 10.1021/acsinfecdis.8b00286.
Li et al, "Antioxidant Activity and Mechanism of Protocatechuic Acid in vitro", Functional Foods in Health and Disease, 2011, 7, 232-244, (Year: 2011).
M.J. Alves et al., "Antimicrobial activity of phenolic compounds identified in wild mushrooms, SAR analysis and docking studies", Journal of Applied Microbiology 115, 346-357, doi:10.1111/jam. 12196.
Mandalari G, "Antimicrobial potential of polyphenols extracted from almond skins", 2010, Letters in Applied Microbiology, 51, 83-89 ( Year: 2010).
Mulay et al., "Cytotoxicity of crystals involves RIPK3-MLKL-mediated necroptosis", Nature Communications, 7:10274, DOI:10. 1038/ncomms10274.
Omid Jalali et al., "Reduced Bacterial Burden of the Skin Surrounding the Shoulder Joint Following Topical Protocatechuic Acid Application", JBJS Open Access d 2020:e19.00078.
Omid Jalali, MD, Molly Best, MD, Alison Wong, MD, Brett Schaeffer, MD, Brendon Bauer, MD, and Lanny Johnson, MD, "Protocatechuic Acid as a Topical Antimicrobial for Surgical Skin Antisepsis", JBJS Open Access, 2020:e19.00079.
Ou C, Shi N, Yang Q, Zhang Y, Wu Z, et al., "Protocatechuic Acid, a Novel Active Substance against Avian Influenza Virus H9N2 Infection", PLoS ONE 9(10): e111004, Oct. 2014.

(Continued)

*Primary Examiner* — Yong S. Chong
(74) *Attorney, Agent, or Firm* — Stonebridge IP, PLLC

(57) ABSTRACT

In embodiments, a method of treating a disease or condition caused by an enveloped virus in a mammal is disclosed including administering to the mammal a composition comprising protocatechuic acid crystals and disrupting the viral envelope of the enveloped virus. The mammal may be a human. The composition may include a pharmaceutically acceptable carrier. The enveloped virus may be a coronavirus. The enveloped virus may be a virus of the family Orthomyxoviridae.

5 Claims, 3 Drawing Sheets

(56) References Cited

OTHER PUBLICATIONS

P. Panthong et al., "Anti-HIV-1 integrase activity and molecular docking of compounds from Albizia procera bark", Pharm Biol, 2015; 53(12): 1861-1866, DOI: 10.3109/13880209.2015.1014568.

R.W. Wood et al., "Spontaneous deformation of protocatechuic acid crystals", Proceedings of the Royal Society of London, vol. 197, A. (Jun. 22, 1949).

Santa Cruz Biotechnology MSDS, "Protocatechuic Acid", sc-205818, (http://datasheets.scbt.com/sc-205818.pdf, Oct. 3, 2009), (Year: 2009).

Wikipedia, "Coronavirus spike protein", last edited on Oct. 16, 2021, at 05:17 (UTC).

Wikipedia, "Coronavirus", last edited on Sep. 11, 2021, at 15:17 (UTC).

Wikipedia, "Drug carrier", last edited on Oct. 16, 2021, at 13:03 (UTC).

Wikipedia, "Essential oil", the free encyclopedia, last edited: Aug. 14, 2021.

F J Lu, S N Tseng, M L Li, S R Shih, "In vitro anti-influenza virus activity of synthetic humate analogues derived from protocatechuic acid", Arch. Virol 2002;147(2):273-84, doi: 10.1007/s705-002-8319-5.

Wikipedia, "Mammal", last edited on Oct. 18, 2021, at 20:36 (UTC).

Wikipedia, "Orthomyxoviridae", last edited on Sep. 12, 2021, at 12:58 (UTC).

Hils J, May A, Sperber M, Klocking R, Helbig B, Sprossig M, "Inhibition of several strains of influenza virus type A and B by phenolic polymers", Biomedica Biochimica Acta, Jan. 1, 1986, 45(9):1173-1179.

Wikipedia, "Protocatechuic acid", the free encyclopedia, last edited Jun. 7, 2021.

Wikipedia, "Viral envelope", last edited on Sep. 16, 2021, at 19:09 (UTC).

Y. Guo, et al., "Protocatechuic acid (PCA) induced a better antiviral effect by immune enhancement in SPF chickens", Microbial Pathogenesis, 114 (2018) 233-238, doi.org/10.1016/j.micpath.2017.11.068.

Wikipedia, "Virus inactivation", last edited on Oct. 22, 2021, at 17:15 (UTC).

Masella et al., "Protocatechuic Acid and Human Disease Prevention: Biological Activities and Molecular Mechanisms", Current Medicinal Chemistry (2012) 19: 2901-2917.

Xiao-Qing Dai, Wen-Tao Cai, Xiao Wu, Yong Chen, Feng-Mei Han, "Protocatechuic acid inhibits hepatitis B virus replication by activating ERK1/2 pathway and down-regulating HNF4α and HNF1α in vitro", Life Sciences, vol. 180, Jul. 1, 2017, pp. 68-74. doi.org/10.1016/j.lfs.2017.05.015.

Sahil Kakkar, Souravh Bais, "A Review on Protocatechuic Acid and Its Pharmacological Potential", Hindawi, International Scholarly Research Notices, vol. 2014, Article ID 952943, 9 pages, 2014, doi.org/10.1155/2014/952943, Abstract.

Semaming Y, Pannengpetch P, Chattipakorn SC, Chattipakorn N, "Pharmacological properties of protocatechuic Acid and its potential roles as complementary medicine", Hindawi Publishing Corp, Evidence-Based Complement Alternative Medicine, vol. 2015, Article ID 593902, doi:10.1155/2015/593902.

Abida Kalsoom Khan et al., "Pharmacological activities of protocatechuic acid", Acta Poloniae Pharmaceutica, Drug Researach, vol. 72 No. 4 pp. 643-650, 2015.

Jiao Song, Yanan He, Chuanhong Luo, Bi Feng, Fei Ran, Hong Xu, Zhimin Ci, Runchun Xu, Li Han, Dingkun Zhang, "New progress in the pharmacology of protocatechuic acid: A compound ingested in daily foods and herbs frequently and heavily", Pharmacological Research, vol. 161, Nov. 2020, 105109.

Jiyang Li, Hai Huang, Meiqing Feng, Wei Zhou, Xun long, ShiPei Zhou, "In vitro and in vivo anti-hepatitis B virus activities of a plant extract from *Geranium carolinianum* L", Antiviral Research, vol. 79, Issue 2, Aug. 2018, pp. 114-120.

\* cited by examiner

METHODS AND COMPOSITIONS INCLUDING PROTOCATECHUIC ACID CRYSTALS FOR THE TREATMENT OF CONDITIONS CAUSED BY AN ENVELOPED VIRUS

CROSS REFERENCE TO RELATED APPLICATIONS

This application is a continuation in part of U.S. application Ser. No. 16/947,256 filed Jul. 24, 2020, which is herein incorporated by reference in its entirety.

BACKGROUND

Technical Field

This disclosure is directed to the use of protocatechuic crystals to destroy enveloped viruses in mammals.

Description of the Related Art

Crystals can provide a therapeutic application by their physical nature. They have known cytotoxic properties which can achieve a therapeutic result. It is known that the physical properties of crystals can have an antimicrobial property independent or in conjunction with biochemical properties. Their many sharp edges have the potential to physically disrupt a microbe's integrity.

Enveloped viruses are particularly physically vulnerable. For example, the covering of the coronavirus, an enveloped virus, is surrounded by many projections like a crown. The projections are called prongs or spikes. These spikes are the virulent contact agent with the host cell. They penetrate the human cell, and the infection is then propagated. The spikes and especially the underlying thin lipid wall coating of the viral body are vulnerable to physical disruption. Physical disruption is one potential method of stopping the encoated virus cellular invasion and the clinical disease. Crystals that have a physical structure that is irregular, rough, and sharp have the potential to physically disrupt a microbes' spikes and covering.

Accordingly, there is a need and an opportunity for prevention and treatment to expand beyond or in conjunction with chemical methods to one that is physical disruption and one that is effective against enveloped viruses.

SUMMARY DISCLOSURE OF THE INVENTION

In embodiments, a method of treating a disease or condition caused by an enveloped virus in a mammal is disclosed including administering to the mammal a composition comprising protocatechuic acid crystals and disrupting the viral envelope of the enveloped virus. The mammal may be a human. The composition may include a pharmaceutically acceptable carrier. The enveloped virus may be a coronavirus. The enveloped virus may be a virus of the family Orthomyxoviridae.

The common denominator of an encoated virus, independent of its causation of differing clinical manifestations or diseases, is the physical vulnerability of the coating or envelope. PCA's therapeutic mode of action is to initially disrupt this inherent weakness and thus is effective against any and all encoated or enveloped viruses.

In embodiments, PCA has a multi-step process of inactivation. The initial disruption is physical based upon the sharp protrusions of the PCA crystal. The inactivation continues in that PCA has a low pH that further destroys the exposed RNA and or DNA. In addition, PCA has anti protease and blocking properties to further limit any surviving encoated virus entry into a cell.

Other features and aspects will be apparent from the following detailed description, the drawings, and the claims.

BRIEF DESCRIPTION OF THE DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DISCLOSURE OF THE INVENTION

Figure 1:
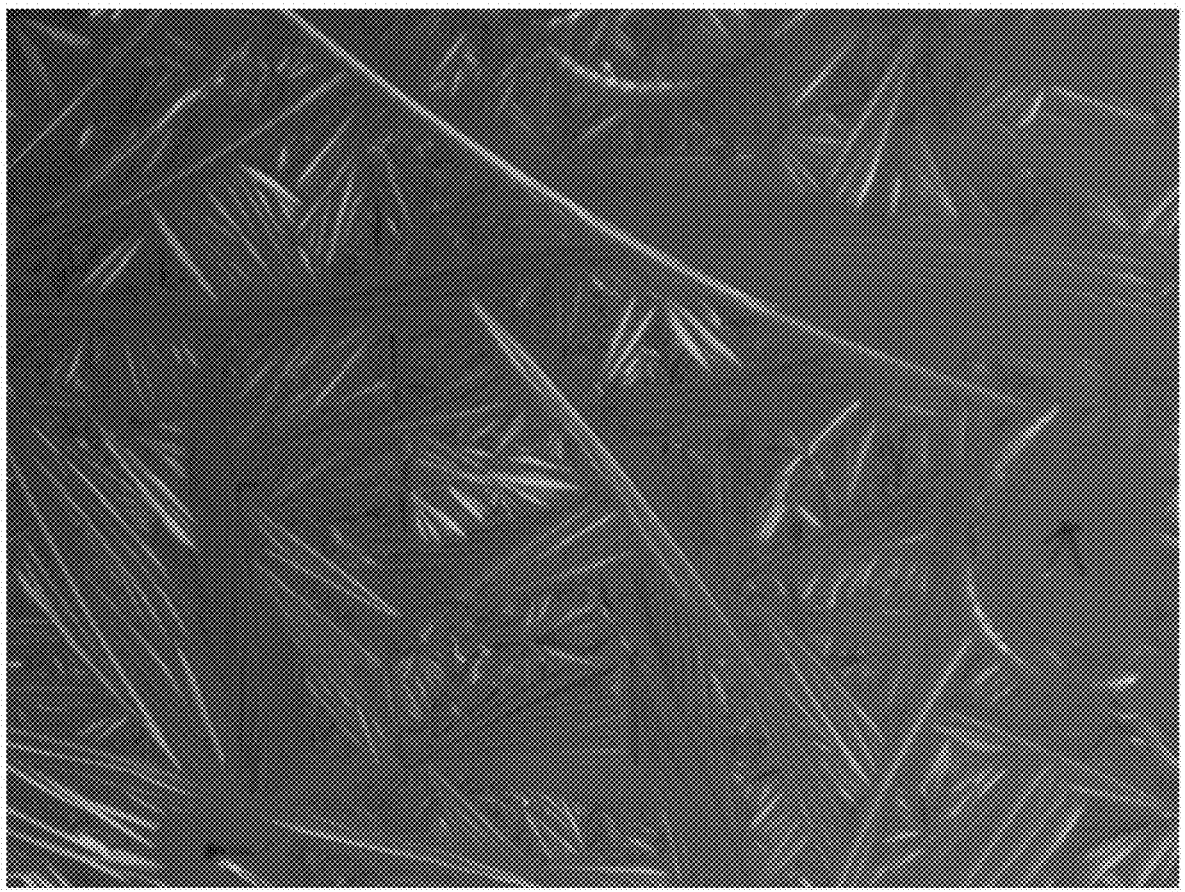
FIG. 1 shows crystals of PCA upon drying on a surface.

The following detailed description is provided to assist the reader in gaining a comprehensive understanding of the methods, products, and/or systems, described herein. However, various changes, modifications, and equivalents of the methods, products, and/or systems described herein will be apparent to an ordinary skilled artisan.

MODES FOR CARRYING OUT THE INVENTION

Viruses are believed to be pieces of nucleic acids from various sources. Viruses are acellular, parasitic entities that are not considered to be alive. They have no plasma membrane, internal organelles, or metabolic processes, and they do not divide. They infect a host cell and use the host's replication processes to reproduce. Viruses infect all forms of organisms including bacteria, archaea, fungi, plants, and animals. Therefore, virus replication is entirely dependent on the host cells.

Viruses are diverse. They vary in structure and target hosts. The structure of all viruses includes a protein shell called a capsid. Enveloped viruses have an additional layer that covers the capsid. An encapsulated virus thus has an envelope that is the outermost layer. This membrane is composed of lipids and proteins. Bumps, knobs, spikes, etc., structures may be present on the envelope.

The envelope protects the virus. Envelopes are typically composed of a thin layer of phospholipid and protein material. The envelope surface serves to identify and bind to receptor sites on the host cell membrane. Enveloped viruses need both an intact capsid and the envelope to infect cells. The envelope also helps avoid detection by the host immune system because it makes the virus appear as any other host cell. The viral envelope fuses with the host's membrane, allowing the capsid and viral genome to enter and infect the host. Enveloped viruses are adaptable and can quickly adapt to evade the immune system. Enveloped viruses can cause persistent infections and must transfer from host to host. Examples of enveloped viruses include many that cause notorious diseases in humans, such as COVID-19, Influenza, Hepatitis B and C, and Hemorrhagic Fever (Ebola Virus Disease), DNA viruses, Herpesviruses, Poxviruses, Hepadnavirus, Asfarviridae, RNA viruses, Flaviviruses, Alphaviruses, Togaviruses, Coronaviruses, Hepatitis D, Orthomyxoviruses, Paramyxoviruses, Rhabdovirus, Bunyaviruses, Filoviruses, Retroviruses, and Retroviruses.

The envelope, however, also provides a soft target for destroying the virus when it is outside the host because the envelope is sensitive to desiccation, heat, soap, and detergents. Therefore, envelope viruses are easier to sterilize than non-enveloped viruses. Common disinfectants, including alcohol, will disrupt the oily envelope and its components destroying the ability for the virus to infect host cells. Enveloped viruses have limited survival outside host environments and typically must transfer directly from host to host. This factor provides a means of mitigation by attacking the virus in transit whether in air or on hard surfaces. Examples of diseases caused by enveloped viruses include ones that cause notorious diseases in humans, such as COVID-19, Influenza, Hepatitis B and C, and Hemorrhagic Fever (Ebola Virus Disease).

Accordingly, although enveloped viruses are highly contagious, the envelope is physically thin and of a fragile material and is vulnerable to physical disruption. The physical nature of protocatechuic acid with sharp needle like protrusions provides a therapeutic mechanism of action by physically disrupting the envelope of encapsulated or enveloped viruses. In embodiments, viruses that can be treated by the present methods and compositions include the family of coronaviruses. Coronaviruses are enveloped viruses of the subfamily Orthocoronavirinae in the family Coronaviridae. More specifically, 229E (alpha coronavirus), NL63 (alpha coronavirus), OC43 (beta coronavirus), HKU1 (beta coronavirus), SARS-CoV (the virus that causes SARS), MERS-COV (the virus that causes Middle East Respiratory Syndrome, or MERS), and SARS-CoV-2 (the virus that causes Covid-19). See Coronavirus, Wikipedia, the free encyclopedia, In embodiments, viruses that can be treated by the present methods and compositions include the family of enveloped influenza viruses Orthomyxoviridae. This includes Alphainfluenzavirus (influenza A virus) including H1N1, H1N2, H2N2, H3N1, H3N2, H3N8, H5N1, H5N2, H5N3, H5N8, H5N9, H7N1, H7N2, H7N3, H7N4, H7N7, H7N9, H9N2, H10N7; Betainfluenzavirus (influenza B virus) including Victoria, Yamagata, Deltainfluenzavirus (influenza D virus), Gammainfluenzavirus (influenza C virus), Isavirus, Thogotovirus including Batken virus, Bourbon virus, Jos virus, and Quaranjavirus.

In embodiments, enveloped viruses that can be treated by the compositions and methods disclosed herein include: gingiva stomatitis, vesicles and ulcers in the mouth, herpes genitalis, vesicles and ulcers on genitalia; herpes labialis, cold sores, fever blisters, vesicles and ulcers of lips, herpes gladiatorum, clusters of vesicles and ulcers on skin, encephalitis, keratoconjunctivitis, whitlow (felon) a purulent infection involving the pulp of the distal phalanx of a finger, Human herpesvirus 3 (varicella-zoster virus), chickenpox (varicella), epithelial cell infection resulting in an exanthem of macules, papules, pustules, vesicles and shallow ulcers shingles (zoster), peripheral nerve cell infection with an eruption in the overlying epidermis Human herpesvirus 4 (Epstein-Barr virus), infectious mononucleosis (b-lymphocyte infection), Burkitt's lymphoma, oropharyngeal carcinoma, Human herpesvirus 5 (cytomegalovirus), cytomegalovirus mononucleosis, infectious mononucleosis, cytomegalic inclusion disease (salivary gland disease), Human herpesvirus 6 (human b-lymphotrophic virus), exanthem subitum (fourth disease, Duke disease or roseola infantum and possibly multiple sclerosis), Human herpesvirus 8, Kaposi's sarcoma in AIDS patients, Human herpesvirus 7, causes a cryptic infection of the T-helper cell Cercopithecine herpesvirus 1 (B virus, herpesvirus simiae), fatal encephalitis, Rubella virus, rubella (German measles), Eastern equine encephalitis virus, encephalitis, Western equine encephalitis virus and encephalitis, Venezuelan equine encephalitis virus, encephalitis, Sindbis virus (fever, rash, arthritis), Semliki forest virus, encephalitis, Chikungunya virus, myositis and arthritis, O'nyong-nyong virus (fever, rash and arthralgia), Ross river virus, (fever, rash, arthralgia), Yellow fever virus, yellow fever, hepatitis, St. Louis encephalitis virus (encephalitis), Dengue virus, dengue, Hepatitis G virus, acute hepatitis via blood transfusions, West Nile virus (fever, rash, hemorrhage and shock), Japanese B encephalitis virus, Japanese encephalitis, Murray Valley encephalitis virus, Murray Valley encephalitis, Central European tick-borne encephalitis virus (encephalitis), Far eastern tick-born encephalitis virus (encephalitis), Kyasanur forest virus, (encephalitis), Louping ill virus (encephalitis), Powassan virus, (encephalitis), Omsk hemorrhagic fever virus (hemorrhagic fever), Kumilinge virus (encephalitis), Absetarov anzalova hypr virus (encephalitis), Ilheus virus (encephalitis), Rocio encephalitis virus (encephalitis), Langat virus (encephalitis), Lymphocytic choriomeningitis virus, lymphocytic choriomeningitis, Junin virus, Argentinean hemorrhagic fever, Bolivian hemorrhagic fever virus, Bolivian hemorrhagic fever, Lassa fever virus, Lassa hemorrhagic fever, Coronavirus, the common cold, Human T-cell lymphotrophic virus, adult leukemia, Human immunodeficiency virus, acquired immunodeficiency syndrome (AIDS), Human foamy virus, California encephalitis virus (encephalitis), Hantaan virus-causes Korean hemorrhagic fever, respiratory/renal disease, Muerto Canyon fever or hantavirus pulmonary syndrome, Bunyamwera virus (encephalitis), Sandfly fever virus (fever, myalgia, retroorbital pain and conjunctivitis), Rift valley fever virus (hemorrhagic fever), Crimean-Congo hemorrhagic fever virus (hemorrhagic fever), Influenza viruses, types A, B, C, influenza Thogotovirus (encephalitis), Parainfluenza virus, parainfluenza, infections of the upper and/or lower respiratory tract, Mumps virus, infections of the parotid gland, Measles virus (rubeola virus), Measles, infection of mucosa and skin epidermal cells, Subacute sclerosing panencephalitis, Respiratory syncytial virus, respiratory syncytial disease, croup Vesicular stomatitis virus, vesicular stomatitis, an infection of the oral mucosa Rabies virus, rabies, an encephalitis Marburg virus (hemorrhagic fever), Ebola virus (hemorrhagic fever).

The disclosure also provides methods and compositions that effectively deliver PCA compositions to an affected mammal including humans. This includes intravenous administration and oral administration including intra nasal, peritoneal, nebulizer, ventilator, and transcutaneous. The present invention also provides compositions and methods for use in the treatment of diseases caused by enveloped viruses to localized affected areas of a mammal as well. This would include the skin, lungs, and nasal cavities. The present disclosure also provides compositions and methods for use in the treatment of a variety of symptoms related to enveloped viruses.

In oral ingestion embodiments, the ready absorption places the PCA in solution in the plasma. As a result, it is known to profuse the entire body; cells, tissues and organs which will kill enveloped viruses on contact. This will last throughout the known presence of PCA in the mammalian body for several days. Additional interval doses over time may give a continued effect. The PCA known metabolism is that it is subsequently found in urine and feces intact and as subsequent metabolites.

In the preferred embodiments of intraperitoneal route of application, the ready absorption places the PCA in solution in the plasma which will kill enveloped viruses on contact. This will last throughout the known presence of PCA in the mammalian body for several days. The PCA known metabolism is that it is subsequently found in urine and feces intact and as subsequent metabolites. Additional interval doses over time may give a continued effect.

In embodiments of intravenous route of application, the administration places the PCA in solution in the plasma which will kill enveloped viruses on contact. This will last throughout the known presence of PCA in the mammalian body for several days. The PCA known metabolism is that it is subsequently found in urine and feces intact and as subsequent metabolites. Additional interval doses over time may give a continued effect.

Also disclosed is a method of treating a pathological condition caused by enveloped viruses, comprising the coating of skin, oral cavity, nares, nasopharynx, and pulmonary tree with PCA in either amorphous or crystalline form.

Also disclosed are methods of treatment of the pathological condition caused by enveloped viruses comprising the intravenous and intraperitoneal route.

In embodiments, the present disclosure provides multiple routes of therapeutic delivery of PCA. Normal size crystals (e.g., approximately 177 μm) and powder may be delivered by the oral route including liquid, or capsule. Smaller sized crystals and particles may also be used for intravenous, intraperitoneal and aerosol delivery to a patient.

The therapeutic compositions and compounds may be administered, for example, orally and topically. The therapeutic compositions and compounds may also be administered by various conventional routes including, for example, oral, topical, buccal, injection, pulmonary, intravenous, inhalant, subcutaneous, sublingual, and/or transdermal.

Further by way of example, the pharmaceutical composition can comprise: PCA and a pharmaceutically acceptable carrier. By way of example, the pharmaceutically acceptable carrier can be selected from, but not limited to, any carrier, diluent, or excipient compatible with the other ingredients of the composition.

Further by way of example, the pharmaceutical composition can comprise PCA and an acceptable delivery carrier. By way of example, the delivery can be formulated and administered as known in the art, e.g., for topical, oral, buccal, including lozenges, injection, intravenous, inhalant, subcutaneous, sublingual and/or transdermal. Further, said topical delivery carrier may be formulated and administered to any surface or cavity of the body.

By way of example, the acceptable delivery can be selected from any dermal or transdermal carrier compatible with the other ingredients of the composition. In some embodiments, the acceptable delivery carrier is a biodegradable microsphere or a slow release bioabsorbable material. By way of example, the acceptable delivery carrier can be selected from 50/50 D, L lactide/glycolide or 85/15 D, L lactide/glycolide, both of which are amorphous physically and, therefore, are non-reactive when used as a carrier in a composition that is delivered in or to the body.

In embodiments, the pharmaceutical composition comprising PCA may be formulated for an aerosol spray. The aerosol spray may include PCA, a liquid vehicle, and a stabilizer. The liquid vehicle may include water, or an alcohol and the stabilizer may include an oil. In preferred embodiments, the oil is an essential oil. In preferred embodiments, the essential oil may be lemon oil. In embodiments, the aerosol spray compositions may comprise principally protocatechuic acid, liquid vehicle, and stabilizer as the main ingredients. In preferred embodiments, the aerosol spray compositions may comprise only protocatechuic acid, a liquid vehicle, and a stabilizer.

An oral dose for humans could be a minimum of 500-1000 milligrams per day. The dose for administration may be interdependent on the other factors. The dose for aerosol spray, ventilation and/or nebulizer, may be a solution. It could be as low as, for example, 25 μM in water. It could be 1 to 30% by weight depending upon a vehicle's solubility properties.

As one example, if it is 1% by weight, then if sprayed 3 times, the resultant dose concentration becomes 3%. If a certain concentration is delivered intravenously the variables include speed of flow and duration.

The inherent impedance of travel varies with the individual so that the amounts delivered to the target, e.g., the lung would depend upon the delivery factors in a ventilator and the fluid, bronchial and alveolar blocked with mucous for example.

One example dosage could be 50 mg/kg, IV, every 6 hours for 4 days.

In aerosol or liquid spray compositions, water may be the vehicle for treatment of mucous membranes of the nose, mouth, pharynx, respiratory tree, and lungs. The compositions may be sprayed, misted, or fogged onto mammalian and human skin, the lungs and/or nasal cavities, etc., to kill and protect from enveloped viruses. Electrostatic means of spraying including sanitizing or disinfection are also included.

Accordingly, in preferred embodiments, the PCA has at least some liquid or moisture present. Preferably, the PCA may be dissolved in water, alcohol, saline, including saline 0.9% salt, or some other liquid, including droplets. Once dissolved in a liquid, the PCA may become crystalline in form and may then physically disrupt a virus and become virucidal. Nevertheless, dry PCA powder in amorphous or crystalline form is also included in this disclosure.

Drugs that change the pH at the surface of a cell membrane inhibit the fusion of the virus to the cell membrane. It can also inhibit nucleic acid replication, glycosylation of viral proteins, virus assembly, new virus particle transport, virus release, and other processes to achieve its antiviral effects. PCA has an acid pH of 5.4 which is disruptive to viral coating and damaging to now exposed contents of RNA or DNA.

COVID-19 main protease (Mpro) is the key enzyme of coronavirus which plays a crucial role in virus replication and transcription, which can be targeted to retard the growth of virus inside the host. One of the major proteins of COVID 19 is Mpro (main protease), also referred to as the '3C-like protease' belonging to the proteases class of hydrolytic enzymes. This enzyme plays a key role in the processing of pp1a (responsible for generating copies of viral genome) and pp1ab (responsible for generating viral genome) as involved in their proteolytic cleavage at the conserved residues among COVID 19 genome.

These can assemble to give rise to virions inside the host cell and thus, replicate to produce multiple copies. Mpro can act as potential target for structure-based drug discovery as this enzyme not only involved in autocatalytic cleavage of itself and key viral enzymes, as well as lacks any close homologues among human hosts. Targeting this enzyme using suitable protease small molecule inhibitor holds immense potential to curb virus replication and transcription which are critical steps in virus life cycle. PCA has antiprotease properties.

Figure 2:
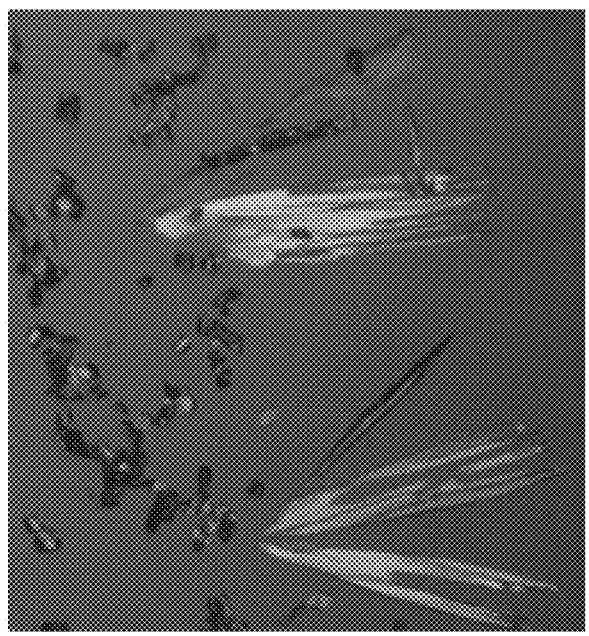
FIG. 2 shows a photomicrograph of crystals of PCA in a water droplet.
Figure 3:
FIG. 3 shows a photomicrograph of crystals of PCA dissolved in ethanol.

FIG. 1 shows crystals of PCA upon drying on a surface. FIG. 2 shows a photomicrograph of crystals of PCA in a water droplet. FIG. 3 shows a photomicrograph of crystals of PCA dissolved in ethanol. The figures show that PCA exists as a crystal upon drying and in solution.

Glossary

Protocatechuic acid (PCA) (IUPAC: 3,4 dihydroxybenzoic acid) is found throughout nature; in the soil and plants. PCA is the primary metabolite of cyanidin-3-glucoside. PCA is common in the human diet in many vegetables and fruits. The human bowel bacteria manufacture small amounts daily. PCA upon ingestion perfuses all the cells and tissues of the human body in matter of a few minutes. The entire metabolism is known with duration of eight hours prior to excretion in the urine and feces.

PCA is safe for human consumption. PCA has an existing FDA G.R.A.S. designation as Generally Recognized As Safe as a flavoring substance. Its FEMA number is 4430. PCA is non-toxic. There are no known allergy or mutagenic effects. PCA is a powerful antioxidant; 10 times more powerful than vitamin E. Antioxidants are fundamental to health. PCA is a powerful anti-inflammatory reagent. Inflammation is known to be the common denominator of all disease. PCA enhanced the genetic expression in vitro studies of local growth factors in human and rabbit synovium, rodent skin and human osteoblasts and mesenchymal stem cells to produce bone. There are known to be many, and varied, health benefits of protocatechuic acid. See protocatechuic acid, Wikipedia, the free encyclopedia, last edited 7 Jun. 2021.

Protocatechuic acid crystals like other crystals are typically observed and considered only in the dry state. However, it known that PCA retains various crystalline shapes while in a liquid medium. The PCA crystal was first reported in liquid to be in three different forms in 1949. A publication from 1949 is extensively illustrated. See Robert Williams Wood; Published: 22 Jun. 1949.

In 1983, Agmon, et al supported Wood's work and showed that some crystalline shapes were stable in form and other were rapidly changing in liquid. See Agmon I, Herbstein F H, Thomas J M, *Spontaneous deformation of protocatechuic acid monohydrate crystals: crystallographic aspects*. Proc., R. Soc. Lond. (1983) A387311-330.

A 'pharmaceutically acceptable carrier' is as described above and is generally any substrate used in the process of drug delivery which serves to improve the selectivity, effectiveness, and/or safety of drug administration. See Drug carrier, Wikipedia, the free encyclopedia, last edited 16 Oct. 2021, herein incorporated by reference.

The term 'mammal' as used herein are a group of vertebrate animals constituting the class Mammalia. Preferably mammal refers to primates and most preferably humans. See Mammal, Wikipedia, the free encyclopedia, last edited 18 Oct. 2021, herein incorporated by reference.

The term 'administration' refers to the administration of a drug to a mammal or human and can be oral; injection into a vein (intravenously, IV), into a muscle (intramuscularly, IM), into the space around the spinalcord (intrathecally), or beneath the skin (subcutaneously), placed under the tongue (sublingually) or between the gums and cheek (buccally), inserted in the rectum (rectally) or vagina (vaginally), placed in the eye (by the ocular route) or the ear (by the otic route), sprayed into the nose and absorbed through the nasal membranes (nasally), breathed into the lungs, usually through the mouth (by inhalation) or mouth and nose (by nebulization), applied to the skin (cutaneously) for a local (topical) or body wide (systemic) effect, delivered through the skin by a patch (transdermally) for a systemic effect. See Drug Administration, Merck Manual, Consumer version, Last full review/revision October 2020, herein incorporated by reference.

A viral envelope refers to the outermost layer of an encapsulated or encoated virus. Bumps, knobs, spikes, etc., structures may be present on the envelope. The envelope protects the virus. Envelopes are typically composed of a thin layer of phospholipid and protein material. The envelope surface serves to identify and bind to receptor sites on the host cell membrane. See Viral envelope, Wikipedia, the free encyclopedia, last edited 16 Sep. 2021, herein incorporated by reference.

An encapsulated virus or encoated virus or enveloped virus is a virus which has a viral envelope.

Viral inactivation renders viruses unable to infect. Viral inactivation stops a virus from contaminating a particular product by rendering them non-infectious. Preferably this is done by chemically altering or physically disrupting a viral envelope. See Virus inactivation, Wikipedia, the free encyclopedia, last edited 22 Oct. 2021, herein incorporated by reference.

EXAMPLE 1

Saliva testing was performed with PCA. This example replicated the practical clinical use of a lozenge to deliver the therapeutic crystals of PCA to the oral cavity and tongue's part of the pharynx and substantiated the lasting duration of PCA coating on those anatomical structure's irregular surfaces of the oral pharynx.

It was initially observed in photomicrographs of PCA powder on glass with polarized light that there were no observable crystals. A human subject then took raw PCA powder into the mouth and allowed for salivation. After approximately 5 minutes a photomicrograph of the saliva/PCA on glass with polarized light showed small black powder and small fluorescent crystals. The fluorescent crystals could be more clearly seen under higher power magnification.

After another approximately 10 minutes, the photomicrographs of the saliva/PCA on glass with polarized light showed more needle shaped crystals. After another approximately 5 minutes, even more needle shaped crystals were visible. There was evidence that the crystals migrated in the fluid by gravity. At this point, a polarized light photomicrograph showed transition shapes although primarily rhomboid, perhaps due to enzymes in the saliva.

Further photomicrographs showed smaller crystals in wet saliva not yet subject to drying. On high power in the wet saliva, powder changing to crystals could be seen with polarized light. That is, there were fewer powder clumps as the powder continued to dissolve and change to crystals. Scraping of the lower lip of the human subject showed the powder had transitioned to crystals that could be seen in polarized light and showed a mixture of rhomboid and needle shapes.

One hour after oral lavage, the human subject tongue was scraped placed on a histology slide and subjected to polarized light showing a multitude of rhomboid and some needle shaped crystals. High-powered photomicrographs showed a single black powder clump surrounded by polarized crystals.

This is representative of a transition from a powder to a crystal in a liquid environment.

EXAMPLE 2

This example shows nasal hair Coating with Protocatechuic acid crystals. The nasal hair has a natural filtering function. Therefore, a PCA coating can be applied with raw crystals, but also with a variety of vehicles; water, glycerin, propylene glycol and or mixtures with alcohols that put the powder into small crystals intimately attached to the hair. Photomicrographs of alcohol solution of PCA on hair with polarized light show the intimacy of crystals on the hair. Photomicrographs show crystals covering the end of the cut hair.

In another experiment, protocatechuic acid crystals from a propylene glycol vehicle were applied to nasal hair. The protocatechuic acid crystals had a different physical appearance at time zero than in the alcohol vehicle of Example 1. This was seen in high power polarized light at junction of fluid and air. There was a vertical line of demarcation. The visualization of the crystals on the hair was delayed for 5 minutes. A propylene glycol coating on the hair and the crystals was evident in the fluid. The shape of the crystals was different from that seen from alcohol vehicle. After a few more minutes crystals were seen on the hair with intimate position. The use of PCA in solution will result in the coating of hair. The use as an adjunct to the mitigation of the SARS CoV 2 virus by coating the hairs of then nares has been demonstrated.

EXAMPLE 3

Example 3 demonstrates the results studies utilizing a methodology replicating the clinical therapeutic environment whereby the PCA crystal engages the SARS CoV-2 virus in an aqueous environment. These studies demonstrate the effectiveness of Protocatechuic Acid (PCA) against SARS-CoV-2, the causative virus for COVID19.

The Test Article (TA) used for this study was Protocatechuic Acid (PCA). The TA was received as an off-white powder. The PCA solution was prepared to be 30% PCA w/v in Ethanol. The PCA was prepared in 5 g increments to pre-warmed 50-60 mL ethanol until dissolved for a total of 30 g PCA in the solution. Additional ethanol was then added volumetrically to be equivalent to 100 mL.

The Test Substrates (TS) were a Plastic-type material sourced from a clear plastic laboratory bottle (Corning 431731 Octagonal bottle, 150 mL), cloth (the top layer of a N95 mask [3M 8210]), and a Sponsor-provided wire mesh to serve as a substrate for the TA. All test substrates were cut to approximately 1"×1" in size. The test substrates were submerged into the PCA solution and dried horizontally to allow for even coating. After the substrate was thoroughly dried, the test substrate was re-submerged into the PCA solution for an additional coating.

The Test Virus used for this study was 2019 Novel Coronavirus, Isolate USA-WA1/2020 (SARS-CoV-2). The virus was stored at approximately ≤−65° C. prior to use. The multiplicity of infection (MOI) was 0.01 $TCID_{50}$/cell.

The Cell Culture used for the $TCID_{50}$ test was African Green Monkey Kidney Cells (Vero E6 cells) that were maintained in Dulbecco's Minimum Essential Medium with 10% fetal calf serum (DMEM-2). All growth media contained heat-inactivated fetal calf serum and antibiotics.

The test design is shown below in Table 1. This test assesses the TA on a substrate in various conditions as shown in Table 1.

The Test Substrate was coated with PCA as described above. The test substrates were treated with PCA twice and allowed to fully dry overnight. In general, the time from the first coat to the next day's virus exposure was approximately 24 hours.

The treated Test Substrate plus TA was placed into a sterile 6 well cell culture plate and approximately 100 μL total of a ≥1×10⁶ $TCID_{50}$/mL SARS-CoV-2 virus was such that 50 μL of virus was layered on each side of the treated test substrates. This was the procedure used for the initial Day 1 experiment.

For the confirmatory test, in an attempt to increase the recorded titer of the controls, the treated Test Substrate plus TA was placed into a sterile 6 well cell culture plate and the same amount of virus was layered onto both sides of the test substrate. However, an addition 50 μL of DMEM was added to each side to reduce the inactivation of the virus due to desiccation. Additionally, a glass coverslip was also added to help mitigate against evaporation.

After application of the virus, the virus was contact with the Test substrates for approximately 10 minutes (Groups 1, 2, and 3, Control groups 7, 8, and 9), 60 minutes (Groups 4, 5, and 6, Control Groups 10, 11, and 12). Each substrate per time per test article was performed in duplicate.

A cell culture-only control was included to indicate that cells without any TA or virus remain healthy throughout the assay. Virus-only controls without substrate was added for each timepoint to verify that the assay was performing as expected.

After the incubation time, the treated substrate was washed with 1 mL of cell culture media (DMEM-2) for approximately 5-10 minutes within the 6 well cell culture plate and the glass cover slip removed if necessary. This was the equivalent to a 10-fold dilution. The plate was gently stirred via an orbital shaker to enhance the recovery of the virus.

For the $TCID_{50}$, the cell culture media (DMEM-2) used to wash the Test Substrate was serially diluted 10-fold and transferred into respective wells of a 96-well plate which contained a monolayer of African Green Monkey Kidney Cells (Vero E6 cells) for titration. The $TCID_{50}$ assay was performed non-GLP according to IITRI Standard Operating Procedures for the assay. The $TCID_{50}$ titers was calculated using the method of Reed-Meunch.

TABLE 1

Study Design

| Group | Test and Control Groups | PCA |
|---|---|---|
| 1 | Plastic (10 minute exposure) | 2 replicates |
| 2 | Cloth (10 minute exposure) | 2 replicates |
| 3 | Mesh (10 minute exposure) | 2 replicates |
| 4 | Plastic (60 minute exposure) | 2 replicates |
| 5 | Cloth (60 minute exposure) | 2 replicates |
| 6 | Mesh (60 minute exposure) | 2 replicates |
| 7 | Virus Control-Plastic (10 minute exposure) | 2 replicates |
| 8 | Virus Control-Cloth (10 minute exposure) | 2 replicates |
| 9 | Virus Control-Mesh (10 minute exposure) | 2 replicates |
| 10 | Virus Control-Plastic (60 minute exposure) | 2 replicates |
| 11 | Virus Control Cloth (60 minute exposure) | 2 replicates |
| 12 | Virus Control Mesh (60 minute exposure) | 2 replicates |

The Test Articles, Test Substrates, and virus (SARS-CoV-2) were prepared according to protocol and each preparation was noted in the study notebook for this study.

Two experimental days were run for this study with the second day as run as a confirmatory. For Day 1, after coating the Test Substrates with PCA as described above (Groups shown in Table 1 above), a $TCID_{50}$ was performed at 10 minutes or 60 minutes after initial application of the virus.

There was an observed log difference between the experimental groups (Group 1: Plastic-10 min, Group 2: Cloth-10 min, Group 3: Mesh-10 min, Group 7: Plastic-60 min, Group 8: Cloth-60 min, Group 9: Mesh-60 min) when compared to the controls (Group 4: Plastic-10 min, Group 5: Cloth-10 min, Group 6: Mesh-10 min, Group 10:Plastic-60 min, Group 11: Cloth-60 min, Group 12: Mesh-60 min)

Day 1 results observed did indicate some log reductions in infectious virus titers under the experimental conditions performed for this study when compared to controls. The results are shown below in Table 2.

TABLE 2

Initial Experimental Run Results.

| Group | Test Article/ substrate | Replicate | Incubation time | $TCID_{50}$ $Log_{10}$/ mL* | Log average | St. Dev. | log difference^ |
|---|---|---|---|---|---|---|---|
| 1 | PCA/plastic | 1 | 10 Min | 3.75 | 3.75 | 0.00 | −0.63 |
|   | PCA/plastic | 2 | 10 min | 3.75 |  |  |  |
| 2 | PCA/Cloth | 1 | 10 min | 2.75 | 2.75 | 0.00 | −1.25 |
|   | PCA/Cloth | 2 | 10 min | 2.75 |  |  |  |
| 3 | PCA/Mesh | 1 | 10 min | 3.50 | 3.38 | 0.18 | −0.25 |
|   | PCA/Mesh | 2 | 10 min | 3.25 |  |  |  |
| 4 | Control/plastic | 1 | 10 Min | 3.75 | 4.38 | 0.88 | N/A |
|   | Control/plastic | 2 | 10 min | 5.00 |  |  |  |
| 5 | Control/Cloth | 1 | 10 min | 3.75 | 4.00 | 0.35 | N/A |
|   | Control/Cloth | 2 | 10 min | 4.25 |  |  |  |
| 6 | Control/Mesh | 1 | 10 min | 3.75 | 3.63 | 0.18 | N/A |
|   | Control/Mesh | 2 | 10 min | 3.50 |  |  |  |
| 7 | PCA/plastic | 1 | 60 Min | 3.25 | 2.88 | 0.53 | −1.13 |
|   | PCA/plastic | 2 | 60 Min | 2.50 |  |  |  |
| 8 | PCA/Cloth | 1 | 60 Min | 2.50 | 2.75 | 0.35 | −1.00 |
|   | PCA/Cloth | 2 | 60 Min | 3.00 |  |  |  |
| 9 | PCA/Mesh | 1 | 60 Min | 1.00 | 1.50 | 0.71 | −2.00 |
|   | PCA/Mesh | 2 | 60 Min | 2.00 |  |  |  |
| 10 | Control/plastic | 1 | 60 Min | 3.75 | 4.00 | 0.35 | N/A |
|   | Control/plastic | 2 | 60 Min | 4.25 |  |  |  |
| 11 | Control/Cloth | 1 | 60 Min | 4.00 | 3.75 | 0.35 | N/A |
|   | Control/Cloth | 2 | 60 Min | 3.50 |  |  |  |
| 12 | Control/Mesh | 1 | 60 Min | 3.25 | 3.50 | 0.35 | N/A |
|   | Control/Mesh | 2 | 60 Min | 3.75 |  |  |  |
| 13 | Virus control (no coupon) | N/A | 10 min | 5.75 | N/A | N/A | N/A |
| 14 | Virus control (no coupon) | N/A | 60 min | 5.75 | N/A | N/A | N/A |

*Limit of detection is 1.5 $TCID_{50}$ $Log_{10}$/mL
^Log difference is defined as the averaged $TCID_{50}$ $Log_{10}$/mL from virus control on substrates - $TCID_{50}$ $Log_{10}$/mL from replicate test group. Log difference indicates amount of reduction in infectious virus when comparing the virus control on substrate to the test group.

For Day 2, after coating the Test Substrates with PCA as described above (Groups shown in Table 1 above), a $TCID_{50}$ was performed at 10 minutes or 60 minutes after initial application of the virus. There was a modification to the procedures to see if the viral titers could be increased. To mitigate against evaporation during the incubation periods, these modifications included adding an additional 50 μl of DMEM on each side of the test substrate and a glass coverslip was placed on top of the test substrate. As with the Day 1 run, there was an observed log difference between the experimental groups (Group 1: Plastic-10 min, Group 2: Cloth-10 min, Group 3: Mesh-10 min, Group 7:Plastic-60 min, Group 8: Cloth-60 min, Group 9: Mesh-60 min) when compared to the controls (Group 4:Plastic-10 min, Group 5: Cloth-10 min, Group 6: Mesh-10 min, Group 10:Plastic-60 min, Group 11: Cloth-60 min, Group 12: Mesh-60 min) as shown in Table 3, thereby confirming the results from the Day 1 run.

TABLE 3

Confirmatory Experimental Run Results.

| Group | Test Article/ substrate | Replicate | Incubation time | $TCID_{50}$ $Log_{10}$/ mL* | Log average | St. Dev. | log difference^ |
|---|---|---|---|---|---|---|---|
| 1 | PCA/plastic | 1 | 10 Min | 4.25 | 4.38 | 0.18 | −1.13 |
|   | PCA/plastic | 2 | 10 min | 4.50 |  |  |  |
| 2 | PCA/Cloth | 1 | 10 min | 4.25 | 4.25 | 0.00 | −1.13 |
|   | PCA/Cloth | 2 | 10 min | 4.25 |  |  |  |

TABLE 3-continued

Confirmatory Experimental Run Results.

| Group | Test Article/ substrate | Replicate | Incubation time | TCID$_{50}$ Log$_{10}$/ mL* | Log average | St. Dev. | log difference^ |
|---|---|---|---|---|---|---|---|
| 3 | PCA/Mesh | 1 | 10 min | 4.75 | 4.63 | 0.18 | −1.13 |
|   | PCA/Mesh | 2 | 10 min | 4.50 |  |  |  |
| 4 | Control/plastic | 1 | 10 Min | 5.50 | 5.50 | 0.00 | N/A |
|   | Control/plastic | 2 | 10 min | 5.50 |  |  |  |
| 5 | Control/Cloth | 1 | 10 min | 5.50 | 5.38 | 0.18 | N/A |
|   | Control/Cloth | 2 | 10 min | 5.25 |  |  |  |
| 6 | Control/Mesh | 1 | 10 min | 5.75 | 5.75 | 0.00 | N/A |
|   | Control/Mesh | 2 | 10 min | 5.75 |  |  |  |
| 7 | PCA/plastic | 1 | 60 Min | 3.50 | 3.63 | 0.18 | −1.50 |
|   | PCA/plastic | 2 | 60 Min | 3.75 |  |  |  |
| 8 | PCA/Cloth | 1 | 60 Min | 2.00 | 2.75 | 1.06 | −2.38 |
|   | PCA/Cloth | 2 | 60 Min | 3.50 |  |  |  |
| 9 | PCA/Mesh | 1 | 60 Min | 4.50 | 4.38 | 0.18 | −0.88 |
|   | PCA/Mesh | 2 | 60 Min | 4.25 |  |  |  |
| 10 | Control/plastic | 1 | 60 Min | 5.00 | 5.13 | 0.18 | N/A |
|   | Control/plastic | 2 | 60 Min | 5.25 |  |  |  |
| 11 | Control/Cloth | 1 | 60 Min | 4.50 | 5.13 | 0.88 | N/A |
|   | Control/Cloth | 2 | 60 Min | 5.75 |  |  |  |
| 12 | Control/Mesh | 1 | 60 Min | 5.25 | 5.25 | 0.00 | N/A |
|   | Control/Mesh | 2 | 60 Min | 5.25 |  |  |  |
| 13 | Virus control (no coupon) | N/A | 10 min | 5.75 | N/A | N/A | N/A |
| 14 | Virus control (no coupon) | N/A | 60 min | 5.75 | N/A | N/A | N/A |

*Limit of detection is 1.5 TCID$_{50}$ Log$_{10}$/mL

^Log difference is defined as the averaged TCID$_{50}$ Log$_{10}$/mL from virus control on substrates - TCID$_{50}$ Log$_{10}$/mL from replicate test group. Log difference indicates amount of reduction in infectious virus when comparing the virus control on substrate to the test group.

TABLE 4

Comparison between Initial Experimental Run to Confirmatory Run

| Test Article/ substrate | Incubation time | Day 1: Log difference | Confirmatory: Log difference |
|---|---|---|---|
| PCA/plastic | 10 Min | −0.63 | −1.13 |
| PCA/Cloth | 10 min | −1.25 | −1.13 |
| PCA/Mesh | 10 min | −0.25 | −1.13 |
| PCA/plastic | 60 Min | −1.13 | −1.50 |
| PCA/Cloth | 60 min | −1.00 | −2.38 |
| PCA/Mesh | 60 min | −2.00 | −0.88 |

A PCA coating on the three test substrates, appeared to show some effectiveness in reducing infectious virus titers in the experimental condition shown in the protocol after the 10 minutes and 60 minutes post-exposure incubation when compared to the virus control on substrate. From both the Day 1 and the confirmatory runs, the log reduction varied between a 0.63 to a 2.38 log reduction.

Overall, these results show that PCA when coated approximately 24 hours prior to virus exposure can reduce infectious virus performance on a substrate, however, overall effectiveness was somewhat varied between runs and test substrate. Additionally, it appears that a longer incubation time may be marginally more effective than the shorter 10-minute time. A 1 to 2 log reduction/difference corresponds to a 90 to 99% inactivation while a 3-log reduction corresponds to a 99.9% inactivation.

EXAMPLE 4

The second laboratory test utilized test coupons made of solid stainless steel, plastic and K95 mask were coated in 30% w/v PCA in 70% ethanol. Each coupon was dipped in PCA, allowed to dry, dipped again, and allowed to dry with the opposite side of the coupon facing up. Once dry, 200 ul virus was added to each coupon and allowed to dry (45 minutes-1 h drying time). Virus was recovered by adding 2 ml DMEM/F12 media and washing the coupon, without scraping so as not to dislodge PCA crystals. A yellow color change in the media was observed indicating acidification of the media upon addition to the PA-coated coupon. The recovered virus was added to empty 96 well plates and diluted 1:10 down the plate. This was then added to Vero E6 cells that had grown to ~70% confluence. Cytotoxicity controls without virus and recovery controls without PCA were also done in the same manner. After addition to the cells, plates were read at day 4 for the presence of cytopathic effect (CPE) due to viral infection of cells. Note that cytotoxicity and CPE cannot be differentiated in this assay, thus any dead cells are marked as positive.

Cytotoxicity was seen up to 1:100 dilution for the K95, and 1:10 for the stainless steel and plastic coupons. Positive CPE for virus recovery controls was seen at least down to 1:10,000 dilutions for all 3 coupon materials, thus each coupon material was adequate for coupon testing. Results are shown in the table below. The SS=stainless steel, K95=K95 mask and P=plastic. +PCA means coupons coated with PCA. No PCA (e.g., SS-1) indicates virus recovery controls with no PCA coating that had virus dried and recovered.

TABLE 5

| Sample Name | Replicate # | TCID50 | TCID50/mL | Log10 TCID50 | Average TCID50 | Average Log10 TCID50 | Log Reduction to Virus Controls | Percent Log Reduction |
| --- | --- | --- | --- | --- | --- | --- | --- | --- |
| SS+PCA-1 | 1 | 501.1872 | 0.01995262 | 2.70 | 298.9493 | 2.37 | 2.93 | 99.88% |
| SS+PCA-2 | 2 | 79.43282 | 0.12589254 | 1.90 | | | | |
| SS+PCA-3 | 3 | 316.2278 | 0.03162278 | 2.50 | | | | |
| SS-1 | 1 | 87992.25 | 0.00011365 | 4.94 | 226075.8 | 5.29 | | |
| SS-2 | 2 | 316227.8 | 3.1623E-05 | 5.50 | | | | |
| SS-3 | 3 | 274007.4 | 3.6495E-05 | 5.44 | | | | |
| K95+PCA-1 | 1 | 316.2278 | 0.03162278 | 2.50 | 182.4589 | 2.10 | 2.45 | 99.65% |
| K95+PCA-2 | 2 | 199.5262 | 0.05011872 | 2.30 | | | | |
| K95+PCA-3 | 3 | 31.62278 | 0.31622777 | 1.50 | | | | |
| K95-1 | 1 | 58230.63 | 0.00017173 | 4.77 | 39285.11 | 4.55 | | |
| K95-2 | 2 | 19952.62 | 0.00050119 | 4.30 | | | | |
| K95-3 | 3 | 39672.07 | 0.00025207 | 4.60 | | | | |
| P+PCA-1 | 1 | 50.11872 | 0.19952623 | 1.70 | 88.00117 | 1.91 | 3.94 | 99.99% |
| P+PCA-2 | 2 | 125.8925 | 0.07943282 | 2.10 | | | | |
| P+PCA-3 | 3 | 87.99225 | 0.11364637 | 1.94 | | | | |
| P-1 | 1 | 1217075 | 8.2164E-06 | 6.09 | 971841.2 | 5.86 | | |
| P-2 | 2 | 203950 | 4.9032E-05 | 5.31 | | | | |
| P-3 | 3 | 1494498 | 6.6912E-06 | 6.17 | | | | |

TABLE 6

The following are the results when the SARS CoV 2 virus was delivered in aqueous droplet on the PCA coated article immediately after drying. The virucidal effect was measured at 2 hours in this test.

| Sample Name | Replicate # | TCID50 | Log10 TCID50 | Average TCID50 | Average Log10 TCID50 | Log Reduction to Virus Controls | Percent Log Reduction |
| --- | --- | --- | --- | --- | --- | --- | --- |
| SS+PCA-1 | 1 | 5.01E+01 | 1.7 | 60.0702 | 1.77 | 2.33 | 99.53% |
| SS+PCA-2 | 2 | 5.84E+01 | 1.77 | | | | |
| SS+PCA-3 | 3 | 7.17E+01 | 1.86 | | | | |
| SS-1 | 1 | 7.94E+03 | 3.9 | 13495.05 | 4.1 | | |
| SS-2 | 2 | 1.26E+04 | 4.1 | | | | |
| SS-3 | 3 | 2.00E+04 | 4.3 | | | | |
| K95+PCA-1 | 1 | 3.16E+01 | 1.5 | 31.62278 | 1.5 | 2.35 | 99.55% |
| K95+PCA-2 | 2 | 3.16E+01 | 1.5 | | | | |
| K95+PCA-3 | 3 | 3.16E+01 | 1.5 | | | | |
| K95-1 | 1 | 5.01E+03 | 3.7 | 7251.46 | 3.85 | | |
| K95-2 | 2 | 7.94E+03 | 3.9 | | | | |
| K95-3 | 3 | 8.80E+03 | 3.94 | | | | |
| P+PCA-1 | 1 | 5.84E+01 | 1.77 | 46.72521 | 1.66 | 2.71 | 99.81% |
| P+PCA-2 | 2 | 5.01E+01 | 1.7 | | | | |
| P+PCA-3 | 3 | 3.16E+01 | 1.5 | | | | |
| P-1 | 1 | 1.26E+04 | 4.1 | 25278.27 | 4.37 | | |
| P-2 | 2 | 3.16E+04 | 4.5 | | | | |
| P-3 | 3 | 3.16E+04 | 4.5 | | | | |

This study shows the continued effectiveness of the PCA coating up to and including 2 hours with a 99%+ Log reduction.

While this disclosure includes specific examples, it will be apparent after an understanding of the disclosure of this application has been attained that various changes in form and details may be made in these examples without departing from the spirit and scope of the claims and their equivalents.

The invention claimed is:

1. A method of inactivating a human enveloped influenza virus type A: H1N1, H1N2, and H3N2; human enveloped influenza virus type B; or human enveloped influenza virus type C comprising:
    orally administering to the human infected with human enveloped influenza virus type A: H1N1, H1N2, and H3N2; human enveloped influenza virus type B; or human enveloped influenza virus type C, a composition consisting of protocatechuic acid crystals; and inactivating the enveloped virus.

2. The method of claim 1, wherein the inactivating step comprises physical disruption of the viral envelope with the protocatechuic acid crystals, and the protocatechuic acid crystals further inactivate exposed RNA and/or DNA via its acidic pH of about 4.5.

3. The method of claim 1, wherein the composition is in a capsule.

4. The method of claim 1, wherein the oral administration dosage of the protocatechuic acid is a minimum of 500 to about 1000 milligrams per day.

5. The method of claim 1, wherein the administration includes 50 mg/kg of the protocatechuic acid up to and at least every 6 hours for 4 days.

* * * * *